United States Patent
Park et al.

(10) Patent No.: US 10,893,894 B2
(45) Date of Patent: Jan. 19, 2021

(54) TRANSVERSE COUPLING FOR SURGICAL IMPLANT EXTENSIONS

(71) Applicant: Aesculap Implant Systems, LLC, Center Valley, PA (US)

(72) Inventors: Jacob Park, Center Valley, PA (US); Andrew Dauster, Center Valley, PA (US)

(73) Assignee: AESCULAP IMPLANT SYSTEMS, LLC, Center Valley, PA (US)

(*) Notice: Subject to any disclaimer, the term of this patent is extended or adjusted under 35 U.S.C. 154(b) by 0 days.

(21) Appl. No.: 16/392,887

(22) Filed: Apr. 24, 2019

(65) Prior Publication Data

US 2020/0337741 A1    Oct. 29, 2020

(51) Int. Cl.
*A61B 17/70*    (2006.01)

(52) U.S. Cl.
CPC ........ *A61B 17/7077* (2013.01); *A61B 17/708* (2013.01); *A61B 17/7049* (2013.01)

(58) Field of Classification Search
CPC .............. A61B 17/7052; A61B 17/705; A61B 17/7049; A61B 17/7077; A61B 17/7079; A61B 17/708
See application file for complete search history.

(56) References Cited

U.S. PATENT DOCUMENTS

| | | | |
|---|---|---|---|
| 4,653,481 A * | 3/1987 | Howland ........... | A61B 17/7001 248/67.5 |
| 5,261,907 A * | 11/1993 | Vignaud ............ | A61B 17/7052 606/60 |
| 5,330,473 A * | 7/1994 | Howland ........... | A61B 17/7049 403/396 |
| 6,585,444 B1 * | 7/2003 | Podbutzky .......... | B25B 23/0035 403/322.1 |
| 7,008,423 B2 | 3/2006 | Assaker et al. | |
| 7,316,425 B2 * | 1/2008 | Poder .................. | F16L 37/0841 285/305 |
| 7,645,294 B2 | 1/2010 | Kalfas et al. | |
| 7,837,714 B2 | 11/2010 | Drewry et al. | |
| 7,875,060 B2 | 1/2011 | Chin | |
| 7,922,747 B2 | 4/2011 | Kirschman | |
| 8,029,543 B2 | 10/2011 | Young et al. | |
| 8,066,743 B2 | 11/2011 | Young et al. | |
| 8,202,302 B2 | 6/2012 | Perez-Cruet et al. | |
| 8,414,617 B2 | 4/2013 | Young et al. | |

(Continued)

FOREIGN PATENT DOCUMENTS

EP    2455031 B1    1/2014

*Primary Examiner* — Jan Christopher L Merene

(57) ABSTRACT

A transverse coupling for connecting multiple implant extensions includes at least a first sleeve and a second sleeve. The first sleeve defines a first aperture adapted to axially receive a first implant extension through the first aperture. The second sleeve defines a second aperture adapted to axially receive a second implant extension through the second aperture. The transverse coupling also includes a central housing. A first shaft connects the first sleeve to the central housing, and a second shaft connects the second sleeve to the central housing. The central housing includes at least one joint for connecting the central housing to at least one of the first and second shafts in a movable arrangement that allows the shaft(s) to move through one or more degrees of freedom relative to the central housing.

25 Claims, 9 Drawing Sheets

(56) References Cited

U.S. PATENT DOCUMENTS

| | | |
|---|---|---|
| 8,585,739 B2 | 11/2013 | Ritland |
| 8,685,062 B2 | 4/2014 | Ritland |
| 8,690,922 B2 | 4/2014 | Ritland |
| 8,784,452 B2 | 7/2014 | Saidha et al. |
| 9,044,273 B2 | 6/2015 | Richelsoph et al. |
| 9,161,781 B2 | 10/2015 | Perez-Cruet et al. |
| 9,232,967 B2 | 1/2016 | Ritland |
| 9,526,531 B2 | 12/2016 | Richelsoph et al. |
| 9,642,650 B2 | 5/2017 | Perez-Cruet et al. |
| 2007/0123860 A1* | 5/2007 | Francis ............. A61B 17/7049 606/250 |
| 2009/0204156 A1* | 8/2009 | McClintock ....... A61B 17/7014 606/278 |
| 2010/0127492 A1* | 5/2010 | Poder ................. F16L 37/0841 285/93 |
| 2010/0174315 A1* | 7/2010 | Scodary ............. A61B 17/7052 606/248 |
| 2010/0249846 A1* | 9/2010 | Simonson .......... A61B 17/8625 606/264 |
| 2012/0035668 A1* | 2/2012 | Manninen .......... A61B 17/7037 606/305 |
| 2012/0083853 A1* | 4/2012 | Boachie-Adjei ... A61B 17/7043 606/86 A |
| 2012/0095512 A1* | 4/2012 | Nihalani ........... A61B 17/7037 606/251 |
| 2012/0130436 A1 | 5/2012 | Haskins et al. |
| 2012/0150230 A1* | 6/2012 | Felix ................. A61B 17/7049 606/250 |
| 2014/0114357 A1* | 4/2014 | Hawkes ............. A61B 17/7014 606/265 |
| 2016/0128734 A1* | 5/2016 | Barlett ............... A61B 17/7052 606/253 |
| 2017/0079687 A1 | 3/2017 | Oberlander et al. |
| 2017/0079690 A1* | 3/2017 | Oberlander ........ A61B 17/7037 |
| 2018/0000522 A1* | 1/2018 | Linares .............. A61B 17/7049 |

\* cited by examiner

TRANSVERSE COUPLING FOR SURGICAL IMPLANT EXTENSIONS

FIELD

The present invention relates generally to surgical instrumentation, and more particularly to a transverse coupling that connects between two surgical implant extensions.

BACKGROUND

Surgical procedures sometimes require the use of a bone implant, a portion of which is attached to a bone inside an incision, and a portion of which extends outside of the patient's body through the incision. For example, a bone implant can be attached to a bone inside an incision, and some type of implant extension can extend outside of the incision. The term "extension" as used herein can refer to any elongated body projecting from a bone implant outside of the patient's body, including but not limited to a long section of the implant that is designed to be broken off of the implant after a procedure is completed, or a separate attachment such as a tube that is detachably connected to the bone implant. One purpose of an extension is to provide a structure than can distribute force on the implant and bone to which the implant is anchored. For example, a force applying instrument can be attached to an extension and manipulated in some manner to apply force to the bone through the extension and bone implant. Such force can be applied to the extension and implant to correct the position or orientation of the bone relative to other bones.

Bone implants with extensions can be used in procedures to correct abnormal curvatures of the spine. In spinal surgery, a pair of bone anchors referred to as "pedicle screws" are attached to each side of a vertebral body. Pedicle screws can be used to apply force to a vertebral body as well as connect the vertebral body to fixation elements, such as a fixation rods. There is often a need to correct abnormal curvatures of the spine by applying a force to multiple pedicle screws at the same time. For example, there may be a need to apply a corrective force to multiple pedicle screws attached to a single level in the spine. At other times, there may be a need to apply corrective force or forces to multiple levels at the same time. In the latter case, there may be a need to apply one force to a pair of pedicle screws at one level, while simultaneously applying another force to another pair of pedicle screws at a different level.

It can be very difficult to apply forces to multiple extensions in a coordinated manner. Each extension extends from the patient at its own unique angle and orientation. Therefore, each extension may require an adjustment force applied in a specific direction that is different from a neighboring extension. The spacing between extensions can also be very limited, making it difficult to attach separate instruments to each extension. Moreover, a procedure that adjusts multiple levels at the same time can be very difficult, as it can require different forces to be applied to four or more extensions simultaneously, in which case two or more surgeons may need to work together in a carefully coordinated manner.

SUMMARY

The inventors have developed an instrument that allows surgeons to apply forces to multiple bone implants in a coordinated but simplified manner. This is achieved by a transverse coupler or bridge that interconnects multiple extensions together. The transverse coupler can be detachably connected to multiple extensions and allow an adjustment force to be applied to the multiple bone implants in a coordinated manner. This permits the surgeon to apply a single adjustment force through the transverse coupler to multiple bone implants at the same time.

In one beneficial aspect of the present disclosure, a transverse coupling is configured for connecting a first implant extension to a second implant extension. The transverse coupling includes a first sleeve, a second sleeve, and a central housing. The first sleeve defines a first aperture adapted to axially receive the first implant extension through the first aperture. The second sleeve defines a second aperture adapted to axially receive the second implant extension through the second aperture. A first shaft connects the first sleeve to the central housing, and a second shaft connects the second sleeve to the central housing.

In another beneficial aspect of the present disclosure, the central housing includes a first joint and a second joint. In this arrangement, the first shaft connects the first sleeve to the first joint of the central housing, and the second shaft connects the second sleeve to the second joint of the central housing.

In another beneficial aspect of the present disclosure, the first joint includes a universal ball joint that is pivotable with respect to the central housing.

In another beneficial aspect of the present disclosure, the universal ball joint includes a longitudinal passage and a plurality of spring sections extending around the longitudinal passage.

In another beneficial aspect of the present disclosure, the first shaft is axially displaceable through the longitudinal passage of the first joint.

In another beneficial aspect of the present disclosure, the first shaft includes a first sleeve end attached to the first sleeve and a first free end opposite the first sleeve end, the first free end including a first stop to limit axial displacement of the first shaft through the longitudinal passage.

In another beneficial aspect of the present disclosure, the first shaft is rotatable in the longitudinal passage of the first joint.

In another beneficial aspect of the present disclosure, the first shaft includes a first shaft cross section with a first abutment face, and the longitudinal passage includes a passage cross section with a first abutment edge. The first abutment edge is configured to abut the first abutment face during rotation of the first shaft relative to the longitudinal passage and limit the range of rotation of the first shaft.

In another beneficial aspect of the present disclosure, the second joint includes a cylindrical through-bore through the central housing.

In another beneficial aspect of the present disclosure, the second shaft is axially displaceable through the through-bore of the second joint.

In another beneficial aspect of the present disclosure, the second shaft includes a second sleeve end attached to the second sleeve and a second free end opposite the second sleeve end, the second free end including a second stop to limit axial displacement of the second shaft through the through-bore of the second joint.

In another beneficial aspect of the present disclosure, the second shaft is rotatable in the through-bore of the second joint.

In another beneficial aspect of the present disclosure, the second shaft includes a second shaft cross section with a second abutment face, and the through-bore includes a through-bore cross section with a second abutment edge, the second abutment edge configured to abut the second abutment face during rotation of the second shaft relative to the longitudinal passage and limit the range of rotation of the second shaft.

In another beneficial aspect of the present disclosure, the central housing includes an upper portion, a lower portion separate from the upper portion, and an adjustment screw extending through the upper portion and the lower portion.

In another beneficial aspect of the present disclosure, the upper portion and the lower portion of the central housing form an adjustable clamp that releasably secures the first shaft in the first joint and releasably secures the second shaft in the second joint.

In another beneficial aspect of the present disclosure, the clamp is adjustable to a locked condition in response to rotation of the adjustment screw, wherein the upper portion and the lower portion of the central housing are drawn together in the locked condition to compress the first joint and the second joint and lock the positions of the first shaft and the second shaft relative to the central housing.

In another beneficial aspect of the present disclosure, the clamp is adjustable to an unlocked condition in response to rotation of the adjustment screw, wherein the upper portion and the lower portion of the central housing are spread apart in the unlocked condition to permit the first shaft and the second shaft to move relative to the central housing.

In another beneficial aspect of the present disclosure, the adjustment screw includes an outer thread and the lower portion of the central housing defines a bore with an inner thread, the outer thread mating with the inner thread.

In another beneficial aspect of the present disclosure, at least one of the first sleeve and the second sleeve defines a sleeve axis and a chamber.

In another beneficial aspect of the present disclosure, at least one of the first sleeve and the second sleeve includes a locking ring defining a locking ring axis, the locking ring being translatable in the chamber in a direction transverse to the sleeve axis.

In another beneficial aspect of the present disclosure, the locking ring is translatable relative to at least one of the first sleeve and the second sleeve between a locking position, in which the locking ring axis is offset from the sleeve axis by a first distance, and a release position, in which the locking ring axis is offset from the sleeve axis by a second distance, the first distance being greater than the second distance.

In another beneficial aspect of the present disclosure, at least one of the first sleeve and the second sleeve includes a spring element in the chamber that exerts a biasing force on the locking ring to urge the locking ring toward the locking position.

In another beneficial aspect of the present disclosure, the locking ring includes a projection extending radially inwardly into the aperture, the projection positioned in the aperture to releasably engage one of the first implant extension and the second implant extension when the locking ring is in the locking position.

In another beneficial aspect of the present disclosure, the locking ring includes a release lug extending radially outwardly and away from the locking ring axis, and at least one of the first sleeve and the second sleeve defines a through-slot into which the release lug extends.

In another beneficial aspect of the present disclosure, the release lug projects through the through-slot in an exposed position in which the release lug is depressible against the biasing force of the spring element to displace the locking ring toward the release position.

In another beneficial aspect of the present disclosure, a transverse coupling is configured for connecting a first implant extension to a second implant extension. The transverse coupling includes a first sleeve, a second sleeve, and a central housing. The first sleeve defines a first aperture adapted to axially receive the first implant extension through the first aperture. The second sleeve defines a second aperture adapted to axially receive the second implant extension through the second aperture. A first shaft connects the first sleeve to the central housing, and a second shaft connects the second sleeve to the central housing. At least one of the first shaft and the second shaft is connected to the central housing by a movable joint on the central housing.

In another beneficial aspect of the present disclosure, the transverse coupling includes a third sleeve defining a third aperture adapted to axially receive a third implant extension through the third aperture. The transverse coupling also includes a third shaft connecting the third sleeve to the central housing.

In another beneficial aspect of the present disclosure, the transverse coupling includes a fourth sleeve defining a fourth aperture adapted to axially receive a fourth implant extension through the fourth aperture. The transverse coupling also includes a fourth shaft connecting the fourth sleeve to the central housing.

BRIEF DESCRIPTION OF THE DRAWINGS

The summary and detailed description sections will be better appreciated when reviewed in conjunction with the drawing figures. The drawing figures illustrate exemplary and non-limiting embodiments of the invention, and depict elements which can be combined and arranged either as shown, or in any other combination and/or arrangement contemplated by persons having ordinary skill in the art.

DETAILED DESCRIPTION

Transverse couplers according to the present disclosure can be attached to two or more extensions mounted on pedicle screws as explained above. For example, a single transverse coupler can be attached to a pair of extensions attached to a vertebral body to maneuver the vertebral body in a procedure referred to as "single level derotation". Alternatively, a first transverse coupler can be attached to a first pair of extensions attached to a first vertebral body, and a second transverse coupler can be attached to a second pair of extensions attached to a second vertebral body. A first force can then be applied through the first transverse coupler to the first pair of extensions, and a second force can be applied simultaneously through the second transverse coupler to the second pair of extensions, to adjust the first and second vertebral bodies relative to one another in single level derotations. Furthermore, transverse couplers can be attached to a block of two or more vertebral bodies to adjust the block of vertebral bodes in an "en bloc" derotation.

Figure 1:
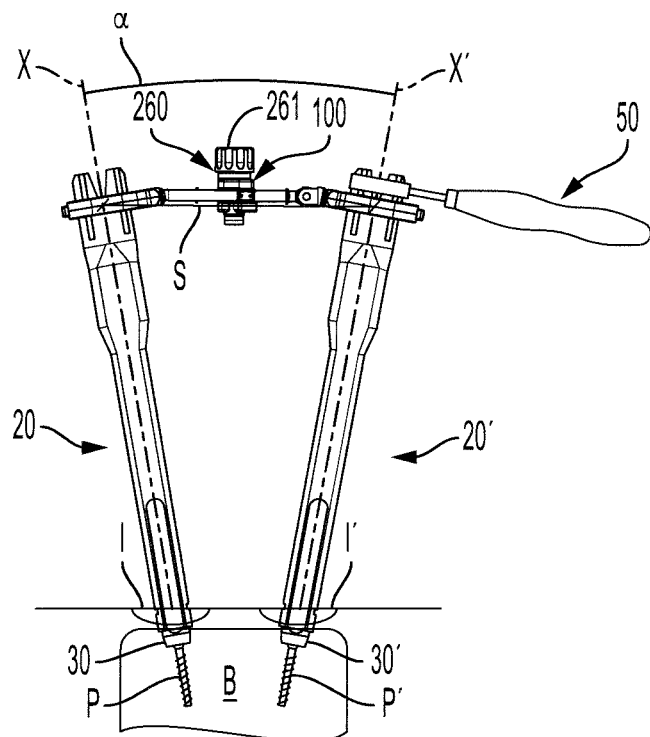
FIG. 1 is an elevation view of a transverse coupler according to one example of the present disclosure, the transverse coupler attached to two extensions that are respectively attached to two bone implants anchored in a bone.

Referring now to the drawings figures, and FIG. 1 specifically, a transverse coupling 100 is shown according to one example. Transverse coupling 100 is detachably mountable to a variety of different bone implants and extensions. As noted above, an extension can be part of the implant itself, or a separate component that is attached to the implant, such as a surgical instrument. In the present example, transverse coupling 100 will be described in combination with a first extension in the form of a first spinal rod persuader 20 and a second extension in the form of a second spinal rod persuader 20'. First spinal rod persuader 20 is attached to a first pedicle screw 30, and second spinal rod persuader 20' is attached to a second pedicle screw 30'.

First pedicle screw 30 is anchored in a first pedicle P of a vertebral body B through a first incision I. Similarly, second pedicle screw 30' is anchored in a second pedicle P' of vertebral body B through a second incision I'. In this arrangement, transverse coupling 100 can receive an adjustment force F from a force applying to instrument 50 and transfer the adjustment force through first and second spinal rod persuaders 20, 20' and first and second pedicle screws 30, 30' to vertebral body B. The transverse coupling 100, rod persuader 20 and rod persuader 20' collectively form a rigid construct. Adjustment forces can be applied directly to this construct or by other instruments attached to this construct. For example, transverse coupling 100 can receive an adjustment force by applying a force directly to one or both of rod persuaders 20, 20'. Alternatively, transverse coupling 100 can receive an adjustment force by applying force to an adjustment screw 260 on the traverse coupling. Force can be applied to adjustment screw 260 through a force applying instrument that attaches to a center knob 261 on the adjustment screw.

First and second pedicle screws 30, 30' are spaced apart and extend from their respective incisions I, I' at different trajectories. Consequently, first and second spinal rod persuaders 20, 20' are also spaced apart and extend from their respective incisions I, I' at different trajectories. The proximal ends of first and second spinal rod persuaders 20, 20' are separated by unique spacing S, and the different trajectories of first and second spinal rod persuaders define an angular offset a between their respective longitudinal axes X, X'.

Transverse coupling 100 has a plurality of adjustable components to accommodate both spacing S and angular offset a between first and second rod persuaders 20, 20'. These adjustable components, which will be described in more detail, are movable relative to one another through one or more degrees of freedom to accommodate an infinite number of spacings and angular offsets between extensions.

Figure 2:
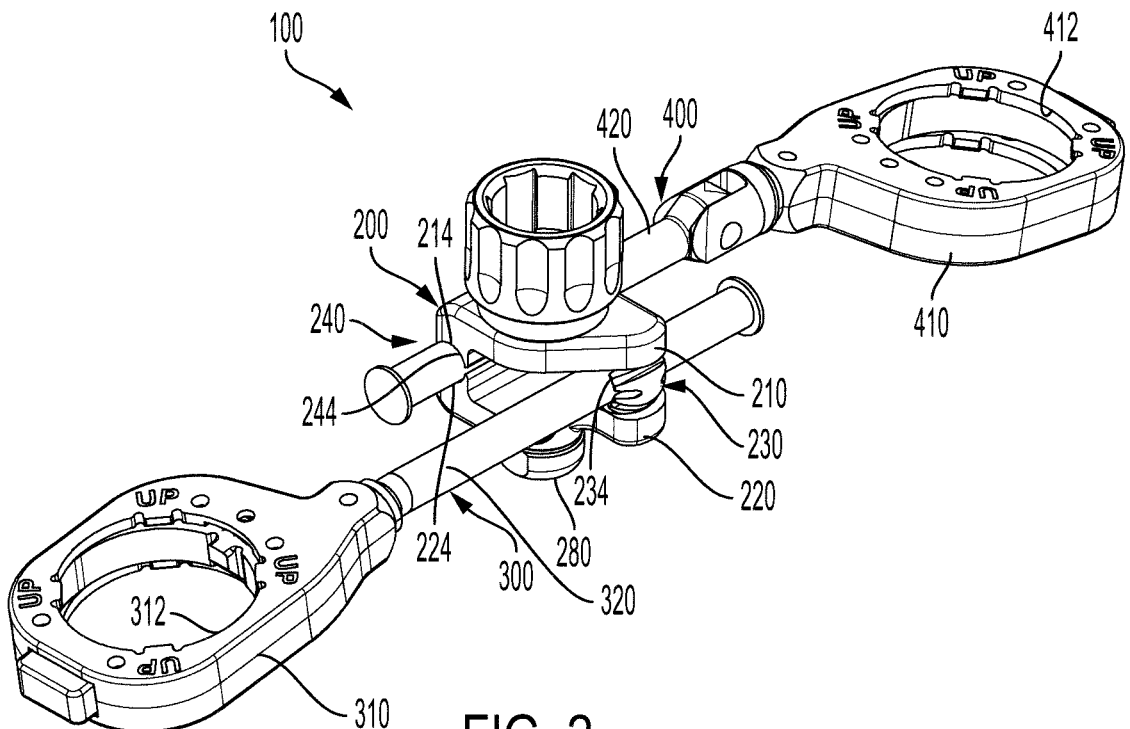
FIG. 2 is a perspective view of the transverse coupler of FIG. 1.
Figure 3:
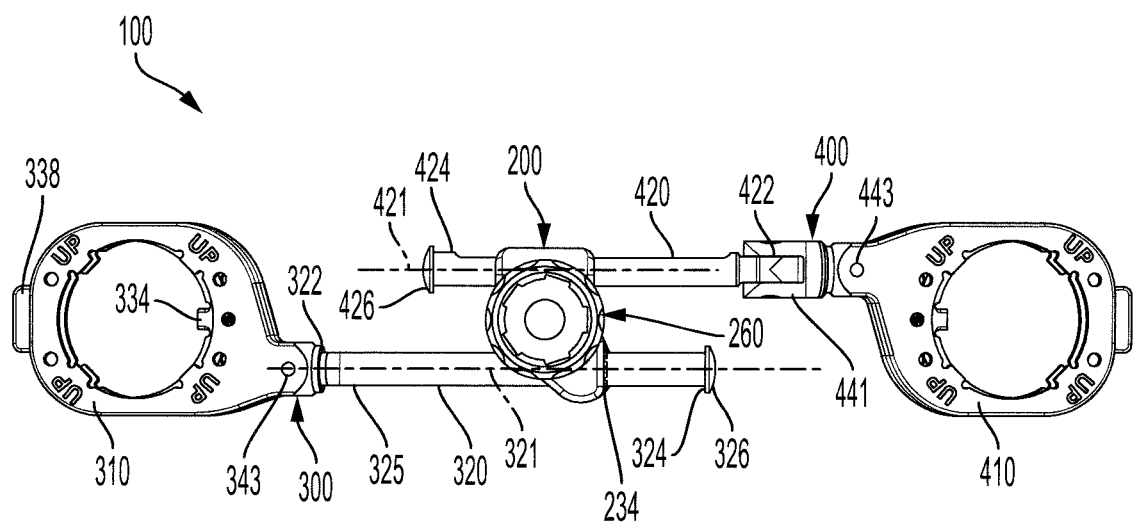
FIG. 3 is a top view of the transverse coupler of FIG. 1.
Figure 4:
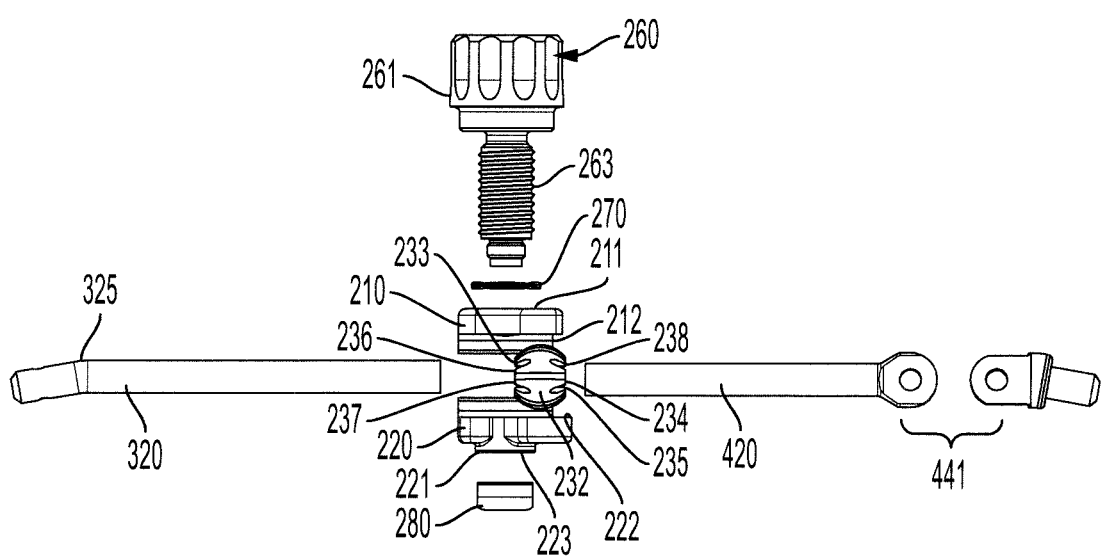
FIG. 4 is an exploded elevation view of components of the transverse coupler of FIG. 1.

Referring to FIGS. 2-4, transverse coupling 100 includes a central housing 200, a first attachment assembly 300 and a second attachment assembly 400. First attachment assembly 300 is detachably mountable to first spinal rod persuader 20, and second attachment assembly 400 is detachably mountable to second spinal rod persuader 20'. Central housing 200 interconnects first attachment assembly 300 and second attachment assembly 400 in an adjustable configuration that allows transverse coupling to adapt to different spacings and angular offsets between extensions.

First attachment assembly 300 includes a first sleeve 310 defining a first aperture 312. First aperture 312 is adapted to axially receive first rod persuader 20 through the first aperture. Transverse coupling 100 also includes a second sleeve 410 defining a second aperture 412 adapted to axially receive second rod persuader 20' through the second aperture. Central housing 200 includes an upper housing portion 210 and a lower housing portion 220. Upper housing portion 210 and lower housing portion 220 are interconnected together in a clamping arrangement. In this clamping arrangement, upper housing portion 210 and lower housing portion 220 define a first joint 230 and a second joint 240.

First attachment assembly 300 includes a first shaft 320 that extends outwardly and away from first sleeve 310. First joint 230 slidably couples first shaft 320 to central housing 200. In a similar arrangement, second attachment assembly 400 includes a second shaft 420 that extends outwardly and away from second sleeve 410. Second joint 240 slidably couples second shaft 420 to central housing 200.

First joint 230 comprises a universal ball joint 232 that is pivotable with respect to the central housing 200. Ball joint 232 defines a longitudinal passage 234 that extends through the ball joint. Longitudinal passage 234 receives first shaft 320 of first attachment assembly 300 in a linear sliding relationship. This linear sliding relationship allows the first shaft 320 to be axially displaceable through longitudinal passage 234 along a first degree of freedom relative to central housing 200. First shaft 320 is also axially rotatable relative to the longitudinal passage 234 in a second degree of freedom.

Ball joint 232 is sandwiched between upper housing portion 210 and lower housing portion 220 of central housing 200. Upper housing portion 210 has a concave bearing surface 212 and lower housing portion 220 has a concave bearing surface 222 opposite concave bearing surface 212. Ball joint 232 slidingly engages bearing surfaces 212, 222 to pivot in place between upper and lower housing portions 210, 220. In this arrangement, ball joint 232 can pivot between upper and lower housing portions 210, 220. When first shaft 320 is received in longitudinal passage 234, the first shaft can pivot through a third degree of freedom relative to central housing 200, which is independent from the first and second degrees of freedom.

Upper and lower housing portions 210, 220 form two halves of a clamp to control displacement of first shaft 320 in first joint 230. In particular, upper and lower housing portions 210, 220 can be clamped together to apply compression force on ball joint 232. Longitudinal passage 234 has a first end 236 and a second end 238 opposite the first end. A first array of slots 233 intersect first end 236 of longitudinal passage 234, and a second array of slots 235 intersect second end 238. Slots 233, 235 form flexible spring sections 237 that surround longitudinal passage 234. Spring sections 237 are compressible under stored energy in a locked state. In the locked state, first shaft 320 cannot move or rotate axially through longitudinal passage 234, and ball joint 232 cannot pivot between upper and lower housing portions 210, 220. When some of the compression force on ball joint 234 is removed, stored energy in spring sections 237 is released, causing the spring sections to expand radially outwardly. As spring sections 237 expand outwardly, they move toward a relaxed state, in which at least some clamping force on first shaft is removed. This removal of clamping force allows first shaft 320 to move axially through longitudinal passage 234. Removal of compression force on ball joint 232 also allows the ball joint to once again pivot between upper and lower housing portions 210, 220 of central housing 200.

First shaft 320 has a first sleeve end 322 attached to first sleeve 310. First shaft 320 also has a first free end 324 opposite first sleeve end 322. First free end 324 includes a first stop 326 to limit axial displacement of first shaft 320 through longitudinal passage 234.

First shaft 320 defines a first shaft axis 321 that is parallel to a longitudinal axis of longitudinal passage 234. When first shaft 320 is not clamped in ball joint 232, the first shaft is rotatable about its longitudinal axis 321 in longitudinal passage 234 in the second degree of freedom.

Second joint 240 comprises a cylindrical through-bore 244 defined between upper housing portion 210 and lower housing portion 220. Upper housing portion 210 forms a concave channel surface 214 and lower housing portion 220 forms a concave channel surface 224. Concave channel surfaces 214, 224 form two halves of through-bore 244 and form the through-bore when upper and lower housing portions 210, 220 are connected together. Second shaft 420 is axially displaceable through through-bore 244 of second joint 240 in a first degree of freedom, similar to first shaft 320 in longitudinal passage 234. In addition, second shaft 420 defines a second shaft axis 421 that is parallel to a longitudinal axis of through-bore 244. As such, second shaft 420 is rotatable about second shaft axis 421 in through-bore in a second degree of freedom.

Second shaft 420 has a second sleeve end 422 attached to the second sleeve 410 and a second free end 424 opposite the second sleeve end. Second free end 424 includes a second stop 426 to limit axial displacement of second shaft 420 through the through-bore 244 of second joint 240.

Shafts according to the present disclosure can rotate the full 360 degrees about their longitudinal axis if desired to adjust the orientation of first their respective sleeves. A full 360 degree rotation is not necessary in many applications, however, because sleeves do not need to be rotated through a large range. Therefore, attachment assemblies according to the present disclosure can feature rotation limiters to limit the range of axial rotation of the shafts.

Figure 5:
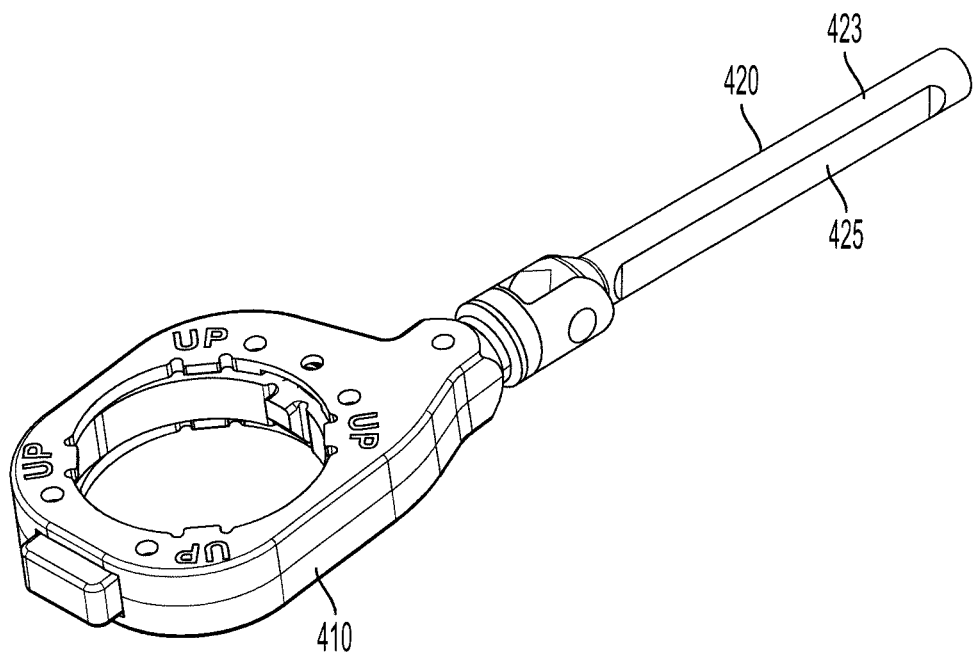
FIG. 5 is a perspective view of a subassembly of components of the transverse coupler of FIG. 4.
Figure 6:
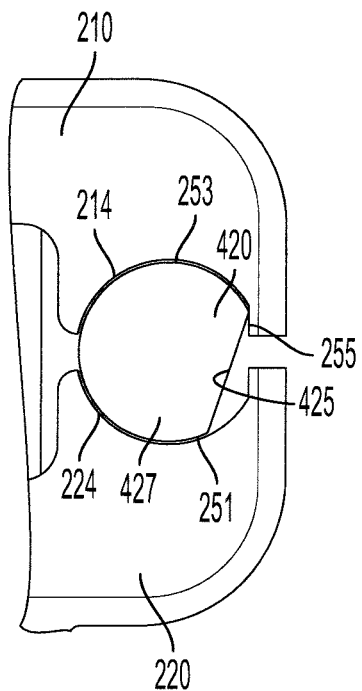
FIG. 6 is a cross section view of components of the transverse coupler of FIG. 1, shown in a first adjustment position.
Figure 7:
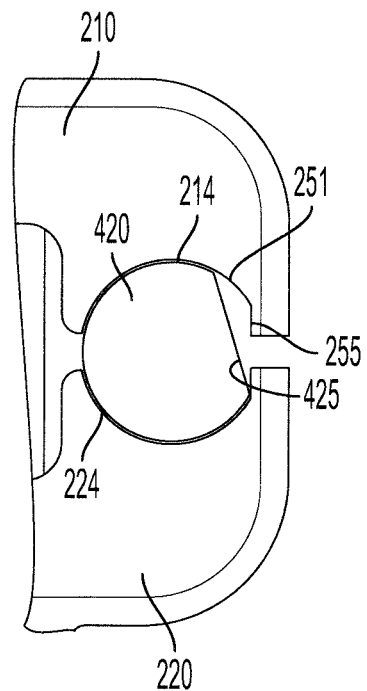
FIG. 7 is a cross section view of the components of the transverse coupler of FIG. 6, shown in a second adjustment position.
Figure 8:
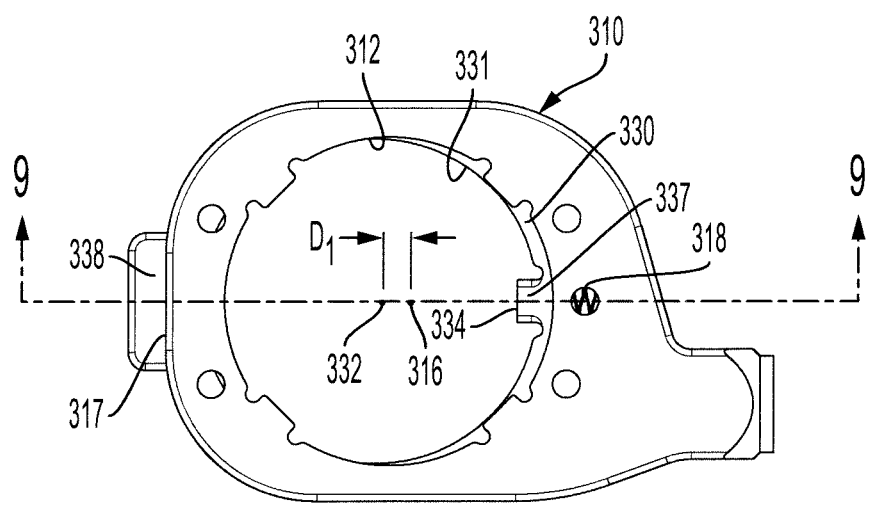
FIG. 8 is a top view of a sleeve of the transverse coupler of FIG. 1 shown in first operative state.
Figure 9:
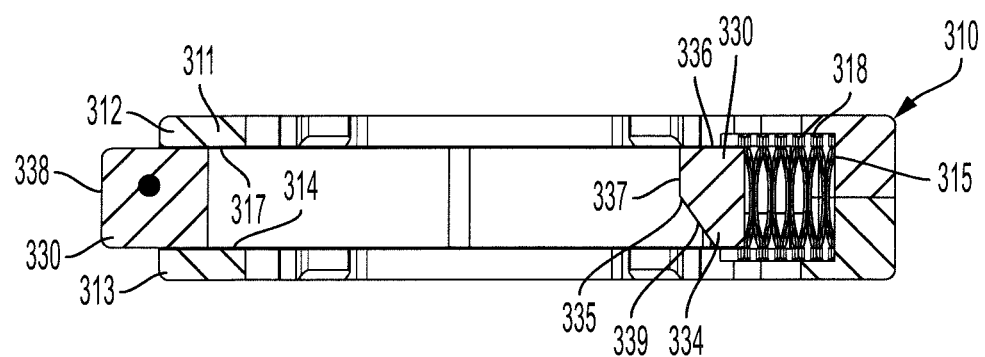
FIG. 9 is a side cross section view of the sleeve of FIG. 8.
Figure 10:
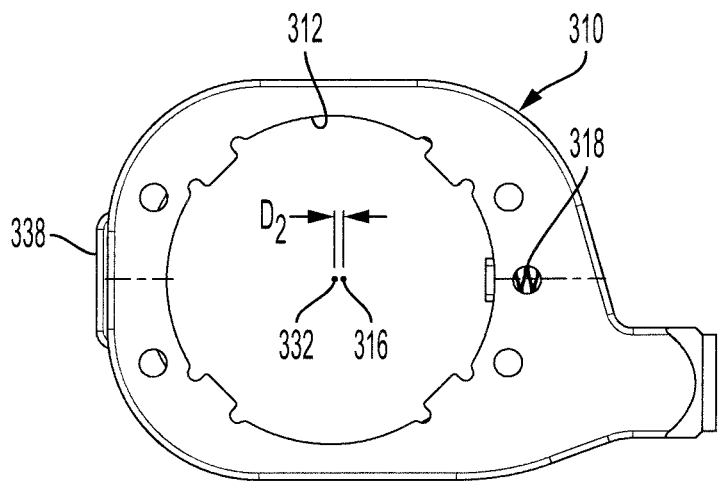
FIG. 10 is a top view of the sleeve of FIG. 8 shown in second operative state.

Referring now to FIGS. 5-7, one example of a rotation limiter is shown between second shaft 420 and through-bore 244. Second shaft 420 has a truncated cylindrical shape that defines a first cylindrical face 423 and a first abutment face 425. First cylindrical face 423 and first abutment face 425 form a shaft cross section 427 in the shape of a truncated circle or "D shape". Through-bore 244 has a similar D-shaped cross section 251 with a first cylindrical edge 253 and a first abutment edge 255. First abutment face 425 is configured to abut first abutment edge 255 during rotation of second shaft 420 relative to through-bore 244. When first abutment face 425 abuts first abutment edge 255, the first abutment edge prevents second shaft 420 from rotating any further in that direction of rotation.

First abutment face 425 can abut first abutment edge 255 in two relative orientations shown in FIGS. 6 and 7. The orientations in FIGS. 6 and 7, which are 40 degrees apart, represent the limits of axial rotation of second shaft 420. Although not shown, it will be appreciated that first shaft 320 and longitudinal passage 234 can have an identical or similar abutment face and abutment edge, respectively, that limit relative rotation of the first shaft through a range of 40 degrees. It will also be appreciated that rotation limiters according to the present disclosure can also be configured to permit smaller or larger ranges of axial rotation, and need not limit rotation to 40 degrees.

Sleeves and shafts according to the present disclosure can be interconnected with fixed joints that fix the orientation of the sleeve relative to the shaft. Alternatively, sleeves and shafts according to the present disclosure can be interconnected with one or movable joints that allow the sleeve to articulate relative to the shaft in one or more degrees of freedom. A movable joint allows a sleeve to be tilted or pivoted in one or more planes relative to its respective shaft to more easily adapt the locking ring aperture to the position and angulation of an extension. In the present example, first sleeve 310 is connected to sleeve end 322 of first shaft 320 with a pin connection 343. Second sleeve 410 is connected to sleeve end 422 of second shaft 420 by a clevis joint 441, which in turn is connected to the second sleeve with a pin connection 443. Sleeve end 322 of first shaft 320 also has a bend 325 that provides a fixed angular offset between free end 324 of the first shaft and first sleeve 310.

Upper housing portion 210 and lower housing portion 220 are interconnected by a fastener that holds the upper housing portion and lower housing portion together in a clamping arrangement. Transverse couplings according to the present disclosure can utilize a variety of fasteners to interconnect the upper and lower housing portions in a clamping arrangement, including but not limited to threaded bolts, cam bolts, and other connectors suitable for drawing the upper and lower housing portions together and spreading them apart. In the present example, upper and lower housing portions 210, 220 are interconnected by an adjustment screw 260, seen best in FIG. 4. Adjustable screw 260 extends through an upper bore 211 that extends through upper housing 210. Upper bore 211 axially aligns with a lower bore 221 in lower housing portion 220 when the upper and lower housing portions are assembled. Lower bore 221 has an inner thread 223 that mates with an outer thread 263 on adjustment screw 260. In this arrangement, adjustment screw 260 is freely insertible in an axial direction through upper bore 211 and into lower bore 221 until outer thread 263 engages inner thread 223 in the lower bore. Adjustment screw 260 can then be rotated to engage outer thread 263 with inner thread 223 and axially advance the adjustment screw into lower bore.

With reference to the top view shown in FIG. 3, adjustment screw 260 can be rotated in a clockwise direction to draw upper and lower housing portions 210, 220 together and into a clamping state. In the clamping state, the first and second shafts 320, 420 completely fixed against all movement relative to central housing 200. That is, the upper and lower housing portions 210, 220 are drawn together such that first shaft 320 is frictionally locked in ball joint 232 and cannot move axially or rotate in any direction relative to the ball joint. In addition, ball joint 232 is compressed by upper and lower housing portions 210, 220 such that the ball joint is frictionally locked between concave bearing surfaces 212, 222 and cannot pivot in any direction between the upper and lower housing portions. Moreover, second shaft 420 is frictionally locked between concave channel surface 214 and concave channel surface 224 so that it cannot move axially or rotate in any direction relative to central housing 200.

Adjustment screw 260 can also be rotated in a counter-clockwise direction to loosen the connection between upper and lower housing portions 210, 220 so that the upper and lower housing portions are in a release state. In the release state, upper and lower housing portions 210, 220 have more freedom to spread apart such that the friction forces on ball joint 232, first shaft 320 and second shaft 420 are minimal and be overcome by applying manual forces on the shafts to move them relative to central housing 200.

Transverse couplings according to the present disclosure preferably include one or more components to prevent the upper housing portion from toggling or moving loosely relative to the lower housing portion and adjustment screw when the upper and lower housings are not in the clamping state. In the present example, a wave spring 270 is inserted between adjustment screw 260 and upper housing portion 210. Wave spring 270 is compressed between adjustment screw 260 and upper housing portion 210 under stored energy. The stored energy in wave spring 270 applies a constant pressure on upper housing portion 210 in the direction of lower housing portion 220 to maintain the upper housing portion in constant contact with first shaft 320 and second shaft 420. This constant contact prevents upper housing portion 210 from toggling, flopping or otherwise moving in a loose manner around adjustment screw 260, even when the adjustment screw is loosened and the upper and lower housings are in the release state.

Transverse couplings according to the present disclosure can also have various components for securing the assembly and preventing disassembly of components. In the present example, a nut 280 is attached to the narrow end of adjustment screw 260 to prevent disassembly of the upper housing portion 210 and lower housing portion 220 from the other components. Nut 280, which is shown in FIGS. 2 and 4, is attached to the narrow end of adjustment screw 260 by welding. It will be understood that various types of fasteners can be used to prevent disassembly. These fasteners can be connected to the adjustment screw by welding, a threaded connection, locking pins or various other types of connection.

Referring now to FIGS. 8-12, the first and second sleeves 310, 410 will be described in more detail. Sleeves 310, 410 are designed to be slipped over a pair of extensions and locked to those extensions to interconnect the extensions together as a unit. Sleeves according to the present disclosure can have one or more design features to accommodate different types of extensions, different types of locking mechanisms or other design variables. In the present example, first and second sleeves 310, 410 are identical, and many of the same components are visible in the drawing figures in both sleeves. Therefore, only features of sleeve 310 will be described, with the understanding that the same features are present in sleeve 410.

First sleeve 310 includes a hollowing housing 311 having an upper housing section 313 and a lower housing section 319. Upper and lower housing sections 313, 319 are connected together to define a hollow chamber 314 between the housing sections. Hollow chamber 314 is substantially enclosed around the perimeter of first sleeve 310 but is open toward first aperture 312. First aperture 312 has a perimeter that conforms to a circle and defines a sleeve axis 316 that passes through the center of the circle.

First sleeve 310 has a floating locking ring 330 housed inside chamber 314. Locking ring 330 is translatable inside chamber 314 between a locking position to lock first sleeve 310 to an extension, and a release position to allow the first sleeve to slide up and down the extension. Locking ring 330 defines an opening 331 having a perimeter that conforms to a circle and a locking ring axis 332 that passes through the center of the circle. Locking ring axis 332 is parallel to sleeve axis 316.

Locking ring 330 is translatable in chamber 314 in a direction transverse to sleeve axis 316. In the locking position, locking ring axis 332 is offset from sleeve axis 316 by a first distance $D_1$, shown in FIG. 8. In the release position, locking ring axis 332 is offset from sleeve axis 316 by a second distance $D_2$, shown in FIG. 10. When locking ring 330 is moved to the locking position, opening 331 is less aligned with first aperture 312. When locking ring 330 is moved to the release position, opening 331 is moved inwardly toward central housing 200, such that the opening is more aligned with first aperture 312. In other words, first distance $D_1$ associated with the locking position is greater than second distance $D_2$ associated with the release position. If desired, locking ring 330 can be arranged in first sleeve 310 in such a way that locking ring axis 332 aligns coaxially with sleeve axis 316 when the locking ring is moved to the release position, in which case second distance $D_2$ would be zero. Locking ring 330 can also be arranged in first sleeve 310 in such a way that locking ring axis 332 moves past sleeve axis 316 to be positioned closer to central housing 200 than the sleeve axis, in which case $D_2$ would be a negative value. Any of these arrangements is suitable so long as the movement of locking ring 310 to the release position moves the projection away from sleeve axis 316 and toward central housing 200.

Figure 11:
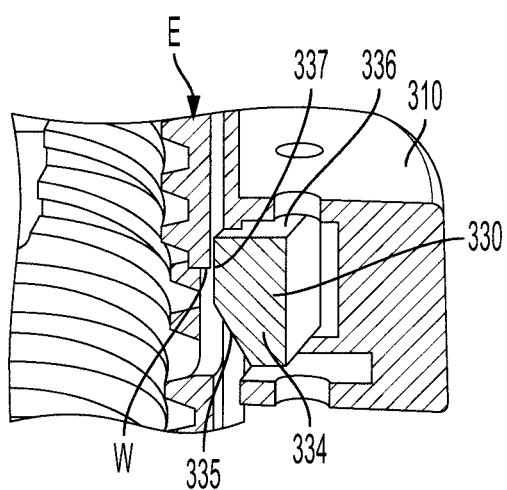
FIG. 11 is an enlarged perspective view in cross section of the transverse coupler of FIG. 1, showing a locking element in a first operative state.

First sleeve 310 includes a spring element 318 in chamber 311. Spring element 318 is held in a compressed state between locking ring 330 and an inner wall 315 of chamber 311. In this arrangement, spring element 318 exerts a biasing force directed radially inwardly toward sleeve axis 316 to urge the locking ring toward the locking position. Sleeves according to the present disclosure can include a variety of spring elements that exert a biasing force on the locking ring, including but not limited to coil springs, disc springs and leaf springs. In the present example, spring element 318 is a wave spring. Locking ring 330 includes a projection 334 extending radially inwardly into opening 331. Projection 334 is positioned to releasably engage a locking feature, such as a locking recess or detent, on an extension when the projection is in the locking position. Projection 334 has leading edge 335, a trailing edge 336 and a sliding edge 337 between the leading edge and trailing edge. Each of edges 334, 335 and 336 plays a role in locking and unlocking first sleeve 310 from an extension. Leading edge 335 is designed to contact the top edge of an extension when first sleeve 310 is initially placed over the top of an extension. During initial placement, locking ring 330 is urged to the locking position by spring element 318, with projection 334 protruding into first aperture 312. Leading edge 335 has a chamfered face 339 that abuts the top edge of the extension as first sleeve 310 is lowered onto the extension. The orientation of chamfered face 339 and the floating arrangement of locking ring 330 cause the locking ring to be deflected against the biasing force of spring element 318 and toward central housing 200 as first sleeve 310 is advanced down the extension. This causes projection 334 to temporarily move out of the locking position to the unlocking position. Locking ring 330 is deflected until sliding edge 337 contacts the outer geometry of the extension. FIG. 11 shows first sleeve 310 and locking ring 330 being advanced down an extension E, with sliding edge 335 abutting the exterior of the extension.

Figure 12:
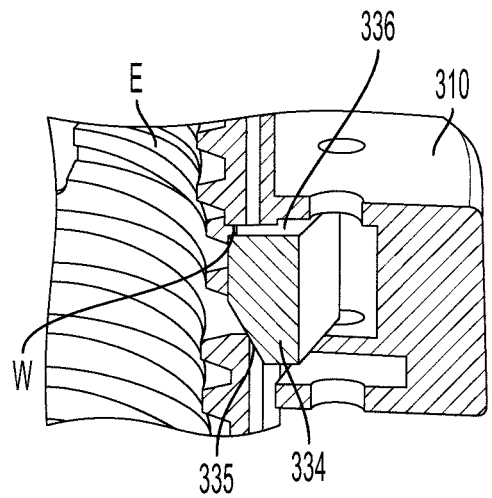
FIG. 12 is another enlarged perspective view in cross section of the transverse coupler of FIG. 1, showing a locking element in a second operative state.

First sleeve 330 can be advanced downwardly around the outer geometry of an extension until the outer geometry of the extension prevent the first sleeve from being advanced any further. For example, the outer geometry of the extension may have a widened section that cannot fit through opening 331 in locking ring 330. The widened section can therefore stabilize first sleeve 330 from moving any further down extension. Extension can further include a cutout or window positioned to engage projection 334 to prevent first sleeve 310 from being inadvertently reversed or moved back up the extension. In such a design, first sleeve 330 is advanced downwardly on the extension until locking ring 330 engages the widened geometry, at which point projection 334 aligns with the cutout or window. The dimensions of the cutout or window are the same as or slightly larger than the dimensions of projection 334, such that the projection can snap into the cutout or window as stored energy in spring element 318 is released. Once projection 334 enters the cutout or window, trailing edge 336 abuts the upper edge of the window, preventing locking ring 330 and first sleeve 310 from moving back up the extension. FIG. 12 shows first sleeve 310 and locking ring 330 further advanced down extension E, with projection 334 snapped inwardly into a window W, and with trailing edge 336 abutting a top edge of the window to prevent the first sleeve from being reversed and moved up the extension.

Sleeves according to the present disclosure can have one or more release mechanisms to move the locking ring out of the locking position and permit the sleeve to be removed from an extension. In the present example, locking ring 330 includes a release lug 338 that extends radially outwardly and away from locking ring axis 332. Sleeve housing 311 defines a through-slot 317 into which release lug 338 extends. Release lug 338 projects out of through-slot 317 in an exposed position on the exterior of first sleeve 310. In this exposed position, release lug 338 is depressible against the biasing force of spring element 318 to displace locking ring 330 toward the release position. This moves projection 334 out of the window or cutout in the extension so that first sleeve 310 is no longer prevented from being lifted and removed from the extension. To remove first sleeve 310 from an extension, a user can depress and hold release lug 338 inwardly toward sleeve axis 316, and lift first sleeve until projection 334 is above the window or cutout. Once projection 334 is above the window or cutout, the user can continue to depress release lug 338 as first sleeve 310 is lifted off the extension. Alternatively, the user can release the release lug 338, at which time sliding edge 337 will abut the exterior of the extension and slide along the outer geometry of the extension until first sleeve 310 is removed.

Although the present disclosure pertains to specific embodiments, the present disclosure is not intended to be limited to the details shown. Rather, various modifications, combinations, substitutions and/or rearrangements can be made with respect to the components and their features shown herein, with any such modification, combination, substitution and/or rearrangement being contemplated within the scope and range of equivalents of the claims and without departing from the present disclosure.

For example, transverse couplings according to the present disclosure can feature a single pair of sleeves with associated shafts interconnected by a central housing, as shown with transverse coupling 100 in FIGS. 2 and 3. Alternatively, transverse couplings according to the present disclosure can feature two or more pairs of sleeves with associated shafts interconnected by central housings. Embodiments with two or more pairs of sleeves with associated shafts and central housings could appear as multiple transverse couplings 100 attached together in parallel. In a parallel arrangement, transverse coupling 100 shown in FIG. 3 could be attached to a second transverse coupling that would appear above it in the Figure, and attached to a third transverse coupling beneath it in the Figure. The three transverse couplings could be interconnected to one another by a connector that interconnects the adjustment screws or other parts of the transverse couplings.

Transverse couplings according to the present disclosure can also feature a single central housing as shown in FIG. 3, but with three or more attachment assemblies connected to the central housing.

Figure 13:
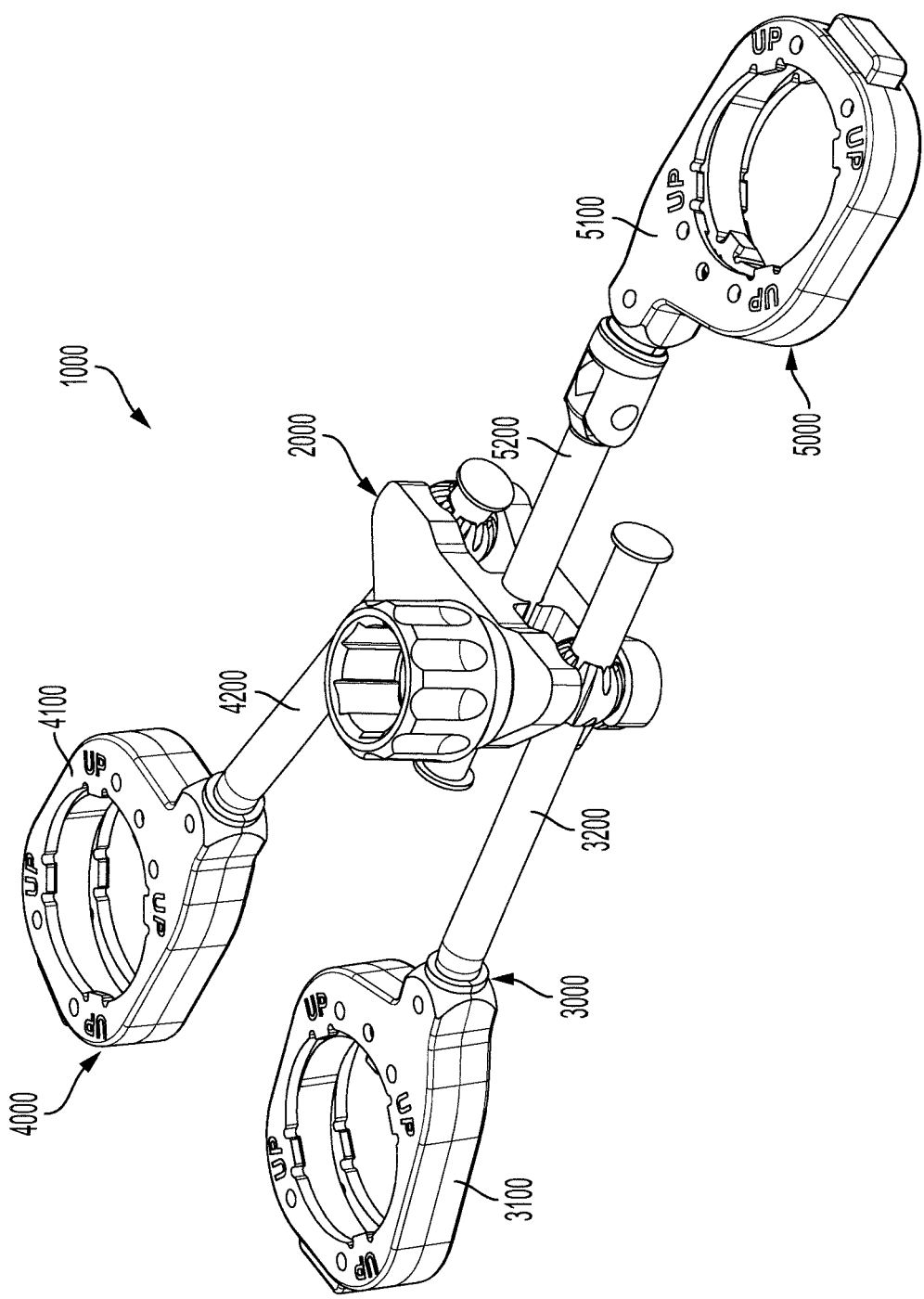
FIG. 13 is a perspective view of a transverse coupler according to another example of the present disclosure.
Figure 14:
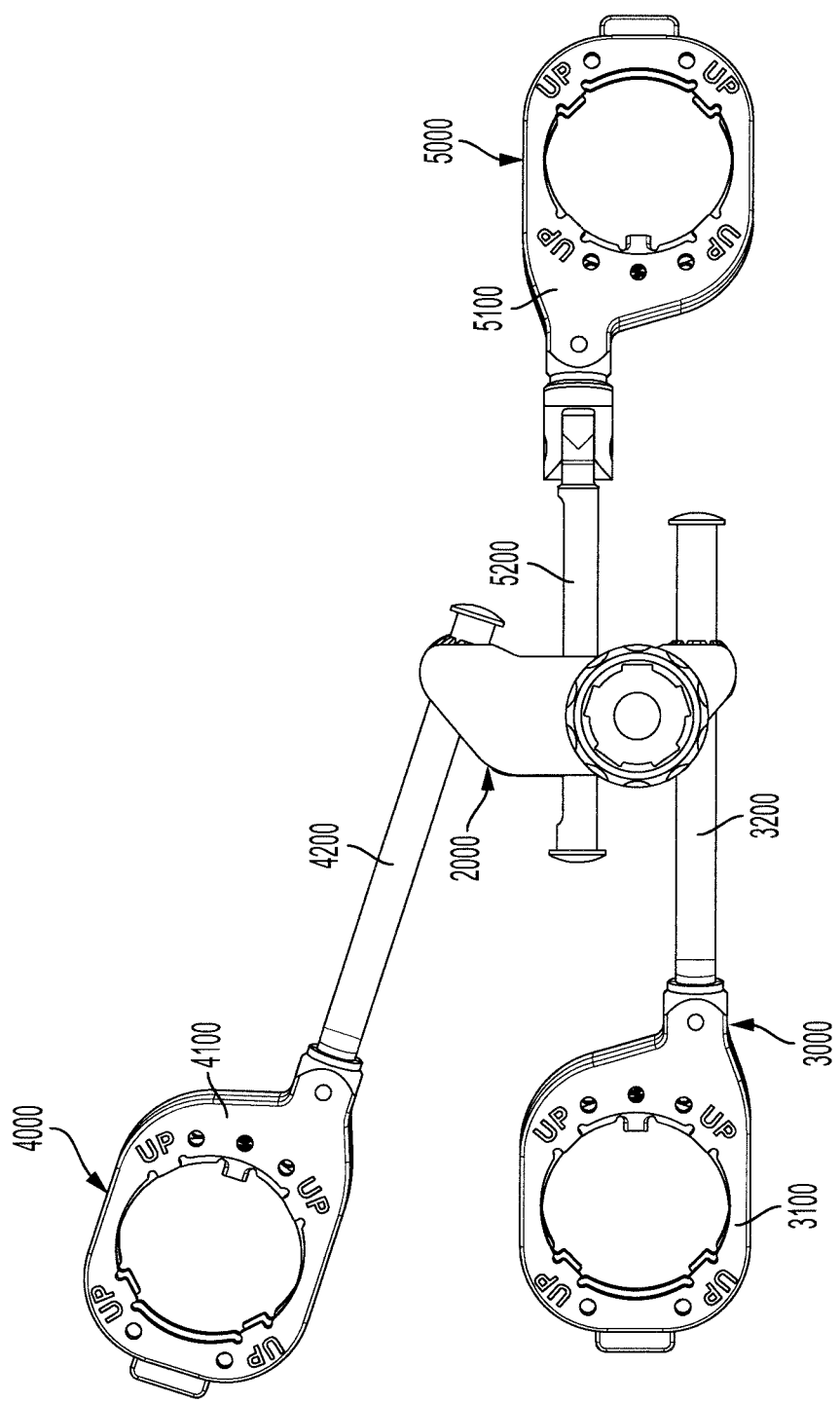
FIG. 14 is a top view of the transverse coupler according to FIG. 13.

For example, FIGS. 13 and 14 show a transverse coupling 1000 with a first attachment assembly 3000 (having a first sleeve 3100 and first shaft 3200), a second attachment assembly 4000 (having a second sleeve 4100 and second shaft 4200) and a third attachment assembly 5000 (having a third sleeve 5100 and third shaft 5200) all connected to a central housing 2000. First, second and third attachment assemblies 3000, 4000 and 5000 are arranged around central housing 2000 to connect the central housing to three different implants or extensions.

Figure 15:
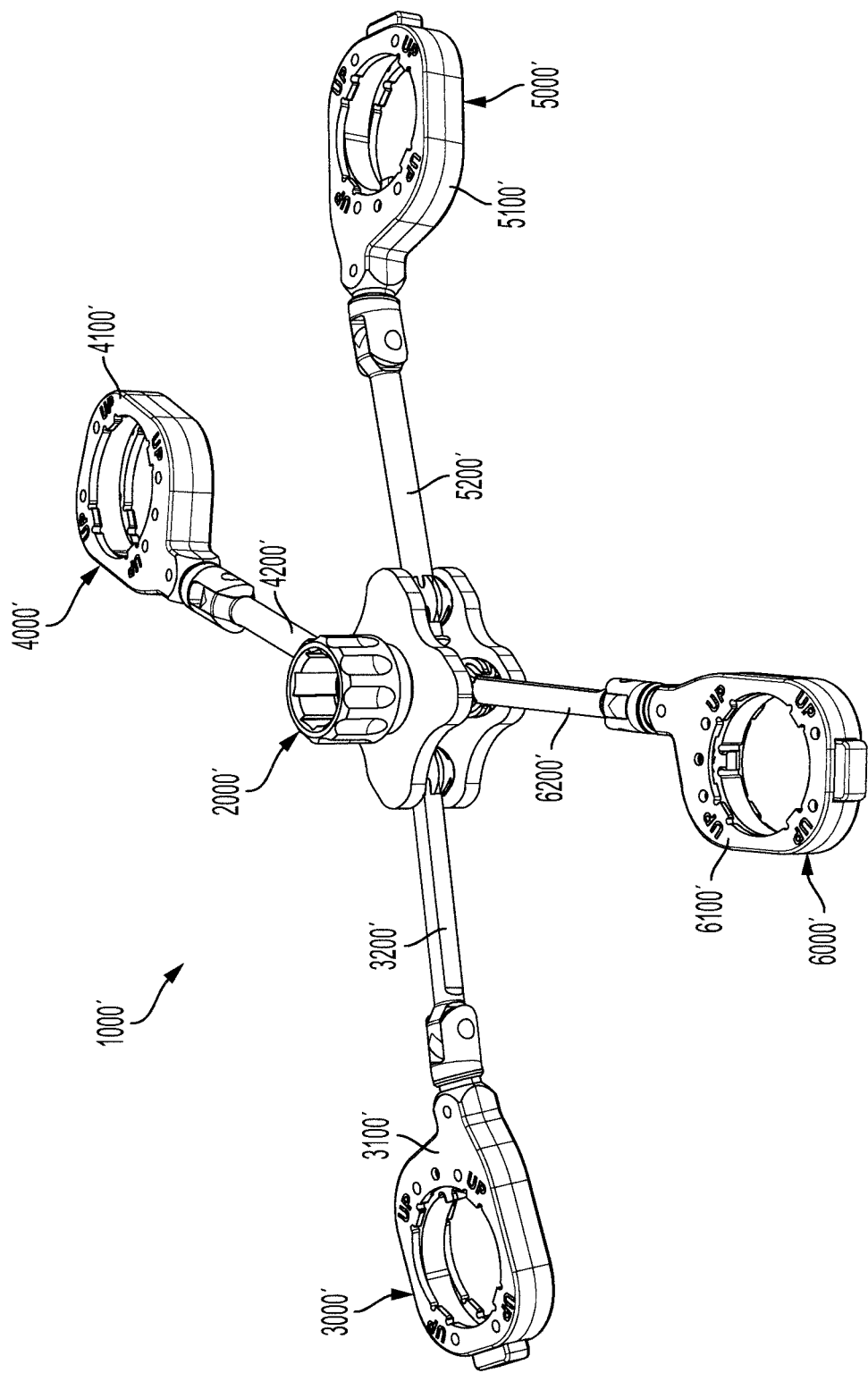
FIG. 15 is a perspective view of a transverse coupler according to another example of the present disclosure.
Figure 16:
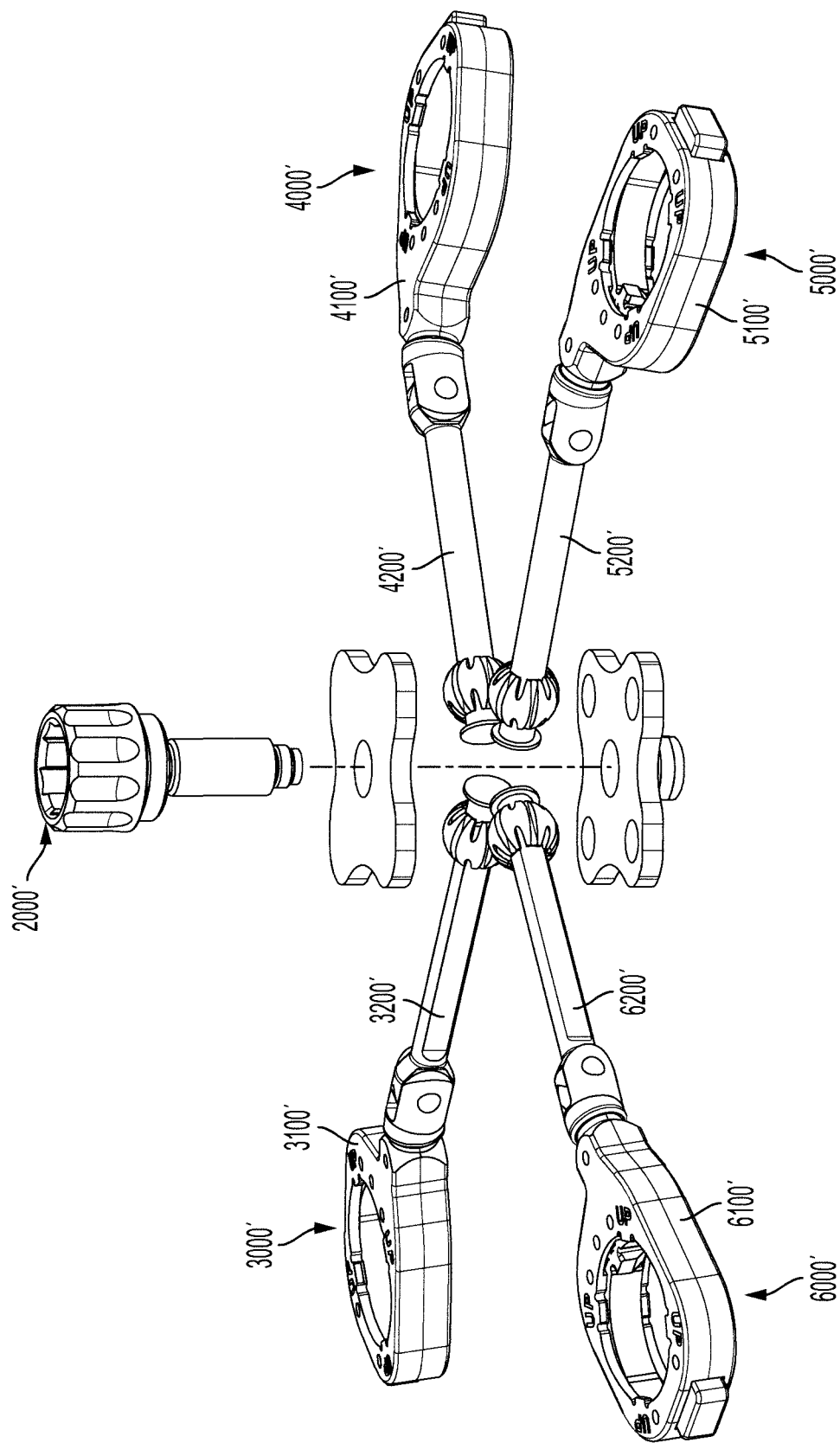
FIG. 16 is an exploded perspective view of the transverse coupler according to FIG. 15.

FIGS. 15 and 16 show another transverse coupling 1000' with a first attachment assembly 3000' (having a first sleeve 3100' and first shaft 3200'), a second attachment assembly 4000' (having a second sleeve 4100' and second shaft 4200'), a third attachment assembly 5000' (having a third sleeve 5100' and third shaft 5200'), and a fourth attachment assembly 6000' (having a fourth sleeve 6100' and fourth shaft 6200') all connected to a central housing 2000'. First, second, third and fourth attachment assemblies 3000', 4000', 5000' and 6000' are arranged around central housing 2000' to connect the central housing to four different implants or extensions.

It will be appreciated that embodiments according to the present disclosure can include five or more attachment assemblies attached to a single central housing. Moreover, it will be appreciated that embodiments according to the present disclosure can have one or more attachment assemblies that are detachably connected to the central housing. Attachment assemblies that are detachable from the central housing permit the transverse coupler to be modified and adapted to the number of implants or extensions that require coupling to a single housing.

What is claimed:

1. A transverse coupling for connecting a first implant extension to a second implant extension, the transverse coupling comprising:
   a first sleeve defining a first aperture adapted to axially receive the first implant extension through the first aperture;
   a second sleeve defining a second aperture adapted to axially receive the second implant extension through the second aperture;
   a central housing comprising a first joint and a second joint;
   a first shaft connecting the first sleeve to the first joint of the central housing, the first shaft having a first diameter; and a second shaft connecting the second sleeve to the second joint of the central housing, the second shaft having a second diameter, the central housing comprising an upper housing portion and a lower housing portion interconnected to the upper housing portion, the upper and lower housing portions forming a first passage through which the first shaft extends and a second passage through which the second shaft extends, the upper and lower housing portions being separated by a first gap that extends alongside the first passage along a first perimeter portion of the central housing, the upper and lower housing portions being separated by a second gap that extends alongside the second passage along a second perimeter portion of the central housing, the first gap being wider than the first diameter of the first shaft so that the first passage is open alongside the first shaft along the first perimeter portion to allow the first shaft to be displaceable relative to the central housing in three degrees of freedom, and the second gap being narrower than the second diameter of the second shaft so that the second gap forms a constriction alongside the second shaft and along the second perimeter portion to limit displacement of the second shaft relative to the central housing to two degrees of freedom and prevent displacement of the second shaft in a third degree of freedom.

2. The transverse coupling of claim 1, wherein the first joint comprises a universal ball joint that is pivotable with respect to the central housing.

3. The transverse coupling of claim 2, wherein the universal ball joint comprises a longitudinal passage and a plurality of spring sections extending around the longitudinal passage.

4. The transverse coupling of claim 3, wherein the first shaft is axially displaceable through the longitudinal passage of the first joint.

5. The transverse coupling of claim 4, wherein the first shaft comprises a first sleeve end attached to the first sleeve and a first free end opposite the first sleeve end, the first free end comprising a first stop to limit axial displacement of the first shaft through the longitudinal passage.

6. The transverse coupling of claim 3, wherein the first shaft is rotatable in the longitudinal passage of the first joint.

7. The transverse coupling of claim 6, wherein the first shaft comprises a first shaft cross section with a first abutment face, and the longitudinal passage comprises a passage cross section with a first abutment edge, the first abutment edge configured to abut the first abutment face during rotation of the first shaft relative to the longitudinal passage and limit the range of rotation of the first shaft.

8. The transverse coupling of claim 1, wherein the second joint comprises a cylindrical through-bore through the central housing.

9. The transverse coupling of claim 8, wherein the second shaft is axially displaceable through the through-bore of the second joint.

10. The transverse coupling of claim 9, wherein the second shaft comprises a second sleeve end attached to the second sleeve and a second free end opposite the second sleeve end, the second free end comprising a second stop to limit axial displacement of the second shaft through the through-bore of the second joint.

11. The transverse coupling of claim 8, wherein the second shaft is rotatable in the through-bore of the second joint.

12. The transverse coupling of claim 11, wherein the second shaft comprises a second shaft cross section with a second abutment face, and the through-bore comprises a through-bore cross section with a second abutment edge, the second abutment edge configured to abut the second abutment face during rotation of the second shaft relative to the longitudinal passage and limit the range of rotation of the second shaft.

13. The transverse coupling of claim 1, wherein the central housing comprises an adjustment screw extending through the upper portion and the lower portion.

14. The transverse coupling of claim 13, wherein the upper portion and the lower portion of the central housing form an adjustable clamp that releasably secures the first shaft in the first joint and releasably secures the second shaft in the second joint.

15. The transverse coupling of claim 14, wherein the clamp is adjustable to a locked condition in response to rotation of the adjustment screw, wherein the upper portion and the lower portion of the central housing are drawn together in said locked condition to compress the first joint and the second joint and lock the positions of the first shaft and the second shaft relative to the central housing.

16. The transverse coupling of claim 14, wherein the clamp is adjustable to an unlocked condition in response to rotation of the adjustment screw, wherein the upper portion and the lower portion of the central housing are spread apart in said unlocked condition to permit the first shaft and the second shaft to move relative to the central housing.

17. The transverse coupling of claim 13, wherein the adjustment screw comprises an outer thread and the lower portion of the central housing defines a bore with an inner thread, the outer thread mating with the inner thread.

18. The transverse coupling of claim 1, wherein at least one of the first sleeve and the second sleeve defines a sleeve axis and a chamber.

19. The transverse coupling of claim 18, wherein said at least one of the first sleeve and the second sleeve comprises a locking ring defining a locking ring axis, the locking ring being translatable in the chamber in a direction transverse to the sleeve axis.

20. The transverse coupling of claim 19, wherein the locking ring is translatable relative to said at least one of the first sleeve and the second sleeve between a locking position, in which the locking ring axis is offset from the sleeve axis by a first distance, and a release position, in which the locking ring axis is offset from the sleeve axis by a second distance, the first distance being greater than the second distance.

21. The transverse coupling of claim 19, wherein said at least one of the first sleeve and the second sleeve comprises a spring element in the chamber that exerts a biasing force on the locking ring to urge the locking ring toward the locking position.

22. The transverse coupling of claim 19, wherein the locking ring comprises a projection extending radially inwardly into the aperture, the projection positioned in the aperture to releasably engage one of the first implant extension and the second implant extension when the locking ring is in the locking position.

23. The transverse coupling of claim 21, wherein the locking ring comprises a release lug extending radially outwardly and away from the locking ring axis, said at least one of the first sleeve and the second sleeve defining a through-slot into which the release lug extends.

24. The transverse coupling of claim 23, wherein the release lug projects through the through-slot in an exposed position in which the release lug is depressible against the biasing force of the spring element to displace the locking ring toward the release position.

25. The transverse coupling of claim 1, wherein the first shaft is connected to the first sleeve at a first sleeve end, the first sleeve end comprising a bend in the first shaft to create a fixed angular offset between the first shaft and the first sleeve.

* * * * *